United States Patent [19]

Cannon et al.

[11] 4,163,063
[45] Jul. 31, 1979

[54] AMINOTETRALIN ADRENERGIC β-AGONISTS

[75] Inventors: Joseph G. Cannon; John P. Long, both of Iowa City, Iowa

[73] Assignee: University of Iowa Research Foundation, Iowa City, Iowa

[21] Appl. No.: 646,300

[22] Filed: Jan. 2, 1976

[51] Int. Cl.$^2$ .................................. A61K 31/135
[52] U.S. Cl. .................................. 424/330; 260/574
[58] Field of Search .................. 424/330; 260/574

[56] References Cited

FOREIGN PATENT DOCUMENTS 2363535  6/1974  Fed. Rep. of Germany .

OTHER PUBLICATIONS

Cannon et al., J. of Med. Chem. (1972), vol. 15, No. 4, pp. 348–350.
W. k. Sprenger et al., J. Med. Chem. (May 1969), vol. 12, pp. 487–490.

Primary Examiner—Stanley J. Friedman
Attorney, Agent, or Firm—Beveridge, DeGrandi, Kline & Lunsford

[57] ABSTRACT

Smooth muscle tissue relaxation is produced in mammals by internal administration of a compound of the formula:

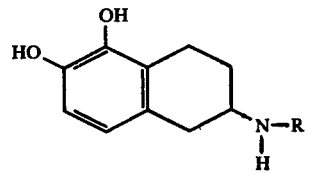

wherein R is alkyl having 1 to 6 carbon atoms, the novel compound 2-N-isopropylamino-1,2,3,4-tetrahydro-5,6,-dihydroxy-naphthalene being preferred. Relief of bronchial asthma and relaxation of the uterine smooth muscle are among the therapeutic effects produced.

8 Claims, No Drawings

AMINOTETRALIN ADRENERGIC β-AGONISTS

The material of this invention was supported by funds from the Department of Health, Education and Welfare.

BACKGROUND OF THE INVENTION

The present invention relates to biologically active compounds which are N-alkyl-substituted derivatives of aminotetralin, and to their therapeutic applications.

Many compounds are known which exhibit adrenergic effects by which term is mean generally a stimulation of nerve fibers mainfested, for example, by nervousness and palpitation.

In 1948, Ahlquist, Am. J. Phyisiol. 135, 586 (1948), demonstrated that the effects of adrenergic drugs appeared to be mediated through two different receptor systems, for which he proposed the names of α- and β-adrenergic receptors. The α-adrenergic receptor was associated mainly with excitatory functions, such as vasoconstriction and stimulation of the uterus, nictitating membrane, ureter, and dilator pupilae, plus an inhibitory function (intestinal relaxation). The β-adrenergic receptor was held to be associated mainly with inhibitory functions, characterized by smooth muscle relaxation in the respiratory tract, uterus, ciliary muscle, and blood vessels in skeletal muscle and liver, plus an important excitatory function, viz. myocardial stimulation.

Lands et al., Nature 214, 597 (1967) demonstrated that β-adrenergic effects can be further subdivided into $\beta_1$ and $\beta_2$ adrenoreceptors. Of these, the $\beta_1$ function includes production lipolysis and cardiac stimulation, indicated by an increase in force and rate of myocardial contraction, and the $\beta_2$ function is indicated by production of bronchial dilatation and vasodepression.

The biological activities of a series of dihydroxy aminotetralins, including the production of emesis in pigeons and dogs, and gnawing in mice, were studied by Cannon et al., J. Med. Chem. 15, 348 (1972). Some of these compounds were found to produce an adrenergic effect similar to that produced by dopamine, 4-(2-aminoethyl)-catechol, namely, to activate dopaminergic receptors. Among the compounds tested was 2-N-methylamino-1,2,3,4-tetrahydro-5,6-dihydroxynaphthalene, in the form of its hydrobromide salt, administered parenterally. However, the only effects noted were the so-called dopaminergic effects, i.e. mouse gnawing, pigeon compulsive pecking response, pigeon and dog emesis.

Further study of certain 2-aminotetralins from the standpoint of their activity as dopamine receptor agonists, was reported by McDermed et al., J. Med. Chem. 18, 362 (1975). The term agonist refers generally to a muscle directly engaged in contraction as distinguished from muscles which have to relax at the same time. Among the derivatives investigated was 2-N-n-propylamino-1,2,3,4-tetrahydro-5,6-dihydroxynaphthalene, the HCl salt of which was reported as melting with decomposition at 231°–233° C. Among the various mono- and di-(lower) alkyl amino derivatives studied, those most consistently productive of apparent dipaminergic activity were the di-n-propylamine derivatives.

Isoproterenol (3,4-dihydroxy-α-[isopropylamino)methyl]-benzyl alcohol is known as sympathomimetic bronchodilator which may produce adrenergic effects. It is widely used because of its rapid onset of action by inhalation. However, in effective dosages, isoproterenol usually activates all β-receptors and often causes cardiac effects because of its ready absorption. It is rapidly taken into cells, and in the lungs (and perhaps elsewhere) it is metabolized by the enzyme catechol-O-methyl transferase, to 3-methyl-isoproterenol, which latter compound is a weak but definite adrenergic β-blocking agent. When isoproterenol is administered orally it is additionally inactivated in the digestive tract and the liver by conversion to a sulfate derivative, which accounts for its relatively short duration of action.

General Description of the Invention

In accordance with the present invention it has been found that β-adrenergic agonist activity is exhibited by aminotetralin compounds of the formula:

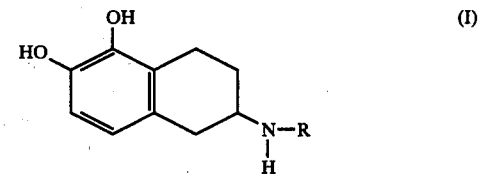

wherein R is alkyl having 1 to 6 carbon atoms.

The substituent R may be, for example, methyl, ethyl, n-propyl, isopropyl, n-butyl, isobutyl, sec.-butyl, tert.-butyl, n-pentyl, isopentyl, or hexyl.

The compounds of formula (I) may be administered therapeutically as the free amine, or in the form addition of salts of pharmaceutically acceptable inorganic or organic acids, such as the hydrochloride, hydrobromide, sulfate, phosphate, acetate, propionate, citrate, benzoate, and the like.

The compounds of formula (I) when administered to mammals all exhibit β-adrenergic agonist effects. It has been found that the methyl-amino and isopropyl amino derivatives are particularly effective, both being much more active as adrenergic β-agonists than the corresponding catecholamine alkyl derivatives, and also much less active than isoproterenol in their ability to lower blood pressure and increase the heart rate.

The preferred compound of the invention is novel compound 2-N-isopropylamino-1,2,3,4-tetrahydro-5,6-dihydroxynaphthalene, as such or in the form of its hydrobromide salt.

The 2-N-alkylamino-5,6-dihydroxytetralin compounds of the invention, as well as the pharmaceutically acceptable and addition salts thereof, have valuable properties as adrenergic β-agonists.

These properties indicate their theraueutic utility for applications which involve relaxation of muscle tissue and especially smooth muscle tissue that is primarily activated by $\beta_2$-receptors, including therapy of bronchial asthma, relaxation of uterine smooth muscle to prevent abortion, relaxation of ureters in patients with kidney stones, and possibly as coronary vasodilators.

In accordance with the present invention, there are provided novel methods for the therapeutic treatment of a mammal requiring such treatment by internally administering to said mammal an amount effective to activate $\beta_2$-receptors whereby to produce smooth muscle relaxation.

The mammals which may be thus treated, within the contemplation, include humans, as well as laboratory animals, for example, dogs, cats, guinea pigs, and rats.

For the foregoing purposes the compounds of the invention may be administered in a therapeutically effective amount, such as to a mammal; orally or parenterally, in a daily dosage from about 5 μg (micrograms) to about 10 mg, per kg of body weight.

For purposes of injection the compounds of the invention can be prepared in the form of solutions, suspensions or emulsions in vehicles conventionally employed for this purpose.

For oral administration, the compounds of the invention may be prepared in aerosol or similar dosage forms suitable for inhalation, or they may be compressed into solid dosage units, such as pills, tablets, lozenges, troches, and the like, with suitable pharmaceutically acceptable diluents, carriers, and adjuvants, or they may be put up in the form of capsules.

The compounds according to the invention exhibit a rapid onset of action, and are highly potent in their activation of $\beta_2$ receptors, being of approximately the same order of activity in this regard as isoproterenol. The relative activity on the heart exhibited by these compounds, as compared to isoproterenol and other selective $\beta_2$ agonists is very advantageous. The compounds of the invention exhibit, when tested on laboratory animals, a 100 to 500 fold separation of $\beta_2$ agonist activity, that is, they have high potency as $\beta_2$ agonists, evidenced by bronchodilation and uterine muscle relaxation, and show only very weak effects on the heart.

The 2-N-alkylamino-5,6-dihydroxy-tetralin compounds of the invention are advantageously prepared by the reductive amination of 5,6-dimethoxy-$\beta$-tetralone by a modification of the method of Borch et al. J.A.C.S. 93, 2897 (1971).

The general method of synthesis, which will be exemplified by the preparation of 2-N-isopropylamino-1,2,3,4-tetrahydro-5,6-dihydroxynaphthalene in the example below, but which is applicable to all the compounds of the character described, is disclosed in the article by McDermed et al. J. Med. Chem., 18, 362 (1975), and is as follows:

2,6-dihydroxynaphthalene is oxidized with $K_2(SO_3)_2NO$ at a pH of 4.5 to 2-hydroxy-5,6,-naphthoquinone, which is converted to 2,5,6-trimethoxynaphthalene by treatment with $Na_2S_2O_4$ and methyl sulfate, and this compound is reduced with sodium and ethanol to 5,6-dimethoxy-$\beta$-tetralone, which is aminated by treatment with an alkylamine and $H_2Pt$ to the 2-N-alkylamino-5,6-dimethoxytetralin compound, which is finally de-etherified with HI and acetic acid to the desired 2-N-alkylamino-5,6-dihydroxytetralin.

The effectiveness of the N-methylamino-and N-isopropylamino-5,6-dihydroxytetralins of the invention is shown by tests on laboratory animals summarized in the following tables:

Cardiac Action

Cats were anaesthetized with pentobarbital sodium, and with both vagi nerves sectioned. The femoral flood pressure was measured, and a cardiotachometer was used to record heart rate changes. The compounds were administered intravenously in dosages from 0.01 to 100 μg/kg. Comparisons were made with isoproterenol and epinephrine, as shown in Table 1:

Table 1

| Relative Potencies in Ability to Increase Heart Rate | | |
|---|---|---|
| Compound | Relative Potency | 95% C.I. *of Potency |
| Isoproterenol | 1 | — |

Table 1-continued

| Relative Potencies in Ability to Increase Heart Rate | | |
|---|---|---|
| Compound | Relative Potency | 95% C.I. *of Potency |
| Epinephrine | 0.095 | 0.064–0.141 |
| N-methylamino cpd. | 0.006 | 0.003–0.009 |
| N-isopropylamino cpd. | 0.002 | 0.001–0.005 |

*Confidence interval

As will be seen from the foregoing table, isoproterenol and epinephrine are much more active in increasing the heart rate than either the N-methylamino derivative or the N-isopropylamino derivative of the invention.

Muscle Relaxation:

As smooth muscle (uterine) relaxants, the N-methylamino derivative and the N-isopropylamino derivative of the invention are approximately equal in their activity, and both possess approximately the same potency as isoproterenol in their ability to activate $\beta_2$ receptors. Using uterine smooth muscle as the $\beta_2$ agonist target organ, the relative potencies were measured in tests on this smooth muscle in rats, the muscle having been previously contracted by treatment with 0.3 μg/ml of methacholine chloride; dosages administered ranged from 0.03 to 10.0 μg/ml/. The inhibitory action was blocked by propranolol, 1 μ/ml. Results are shown in Table 2:

Table 2

| Relative Potencies in Relaxation of Uterine Smooth Muscle | | |
|---|---|---|
| Compound | Potency Ratio | 95% C.I. |
| Isoproterenol | 1 | — |
| N-methylamino cpd. | 1.02 | 0.43–2.41 |
| N-isopropylamino cpd. | 0.34 | 0.09–0.84 |

Table 2 indicates that all three compounds exhibit similar activity in their ability to relax the isolated rat uterine muscle preparation. The animals were pretreated with estrogen, and the ability to relax the resulting spontaneous contractions was used as the criterion.

Blood Pressure

In further tests on the aminotetralin derivatives of the invention, as compared with their open-chain analogs, for their cats with both vagi nerves sectioned, and for their ability to relax tracheal smooth muscle of guinea pigs, it was found that the N-isopropylamino derivatives exhibits only $\beta$receptor activation, while the N-methylamino compound activates $\beta$receptors at lower doses and simultaneously activates $\alpha$receptors at high doses, i.e. it produces both $\alpha$ and $\beta$ adrenoceptor stimulating activity. The $\beta$-adrenoceptor stimulating activities of both the N-methylamino compound and the N-isopropylamino compound showed more specificity for $\beta_2$ adrenoceptors than for $\beta_1$ adrenoceptors.

In tests on blood pressure and heart rate, cats weighing between 2 and 4 kg were anaesthetized by intraperitoneal administration of pentobartibal sodium, 30 mg/kg. After endotracheal intubation, artifical respiration was maintained with a Harvard ventilator and both vagi nerves were cut. Arterial blood pressure was measured using transducer attached to a cannula inserted into the left femoral artery; a cannula was inserted into the right femoral vein for intravenous drug administration. Blood pressure was recorded with a Beckman R recorder. The heart rate was monitored with a Beckman cardiotachometer.

Tracheal Muscle Relaxation

In tests on isolated guinea pig tracheal chain preparations six tracheal rings were used for a chain. The chains were suspended in a 15 ml organ bath containing Krebs solution. The solution contained 200 μg/ml ascorbic acid to suppress oxidation of the compounds. The bath medium was gassed with 95% $O_2$–5% $CO_2$ and maintained at 37° C., applied resting tension to preparation was 0.5 gram. Contractions and relaxations were measured by using a strain gage and recorded. Methacholine chloride was used to induce contractions.

The relative potencies (at 95% confidence interval) of the various compounds in their ability to increase the heart rate of cats and to relax the tracheal muscle of guinea pigs are shown in Table 3:

Table 3

Relative Potencies to Increase Heart Rate of Cats and Tracheal Muscle Relaxation of Guinea Pigs

| Compound | Heart Rate Increase (in vivo) | Tracheal Muscle Relaxation (in vitro) |
| --- | --- | --- |
| Isoproterenol | 1.00 | 1.00 |
| Ephinephrine | 0.153 (0.099–0.223) | 0.28 (0.22–0.37) |
| N-methylamino cpd. | 0.005 (0.002–0.007) | 0.59 (0.42–0.82) |
| N-isopropylamino cpd. | 0.002 (0.001–0.004) | 2.70 (1.81–3.95) |

Unexpectedly, on isolated guinea pig tracheal chain preparation, the N-isopropylamino derivatives was found more active than isoproterenol.

In tests on blood pressure (cats), the N-isopropylamino compound produced decreases, whereas the N-methylamino compound produced biphasic responses: lower doses decrease blood pressure, but higher doses showed a pressor response. Results for lowering blood pressure are shown in Table 4:

Table 4

Relative Potencies to Decrease Blood Pressure in Cats

| Compound | Minimal Dose for Assay (μg/kg) | Diastolic Pressure Decrease |
| --- | --- | --- |
| Isoproterenol | 0.05 | 1.0 |
| N-methylamino cpd. | 1.0 | 0.08 (0.05–0.3) |
| N-isopropylamino cpd. | 2.0 | 0.019 (0.006–0.05) |

DESCRIPTION OF THE PREFERRED EMBODIMENTS

The following example describes the preparation of the N-isopropylamino derivative, but is to be regarded as illustrative, and not as limiting:

EXAMPLE 1

Preparation of 2-N-isopropylamino 1,2,3,4-tetrahydro-5,6-dihydroxynaphthalene

Tetrahydro-5,6-dimethoxy-2(1H)-naphthaleneone (7.0 g, 0.038 mol), prepared as described by Cannon et al., J. Med. Chem. 17, 565 (1974), dissolved in 45 ml of MeOH, was added with stirring to 13.5 g (0.22 mol) of isopropylamine in 45 ml of MeOH and 15 ml of 5N methanolic HCl and the resulting mixture was cooled under $N_2$ in an ice bath. Sodium cyanoborohydride (1.52 g, 0.0228 mol) was added, to give a purple reaction mixture. Methanolic HCl was added carefully until the purple color changed to yellow-brown, and during the course of the reaction, more was added to maintain the yellow-brown color. At the end of 3 hrs stirring at room temperature, the reaction mixture was brought to pH 2 with concentrated HCl. Volatiles were removed under reduced pressure, and the residue was taken up with water. This solution was extracted three times with $Et_2O$,[2] then was basified with KOH and extracted with $Et_2O$. This extract was dried ($Na_2SO_4$), filtered, and the filtrate was treated with ethereal HCl. The solid which separated was recrystallized 3 times from EtOH[3]-EtOH-$Et_2O$ and once from 2PrOH[4]-$Et_2O$ to yield w.1 g (19%) of material, mp 251°–252° C. Analysis: $C_{15}H_{24}ClNO_2$. The compound was 1,2,3,4-tetrahydro-2-isopropylamino-5,6-dimethoxynaphthalene hydrochloride.

[1] Methanol [2] Diethyl ether [3] Ethanol [4] Propanol

The foregoing compound was heated in excess 48% HBr under nitrogen for 3 hours at 150° C. Volatiles were removed under reduced pressure (steam bath), and the crude HBr salt was recrystallized from EtOH-$Et_2O$. The yield was 84%, the analysis $C_{13}H_{20}BrNO_2$, mp. 129°–130° C. (decomp.). The compound was the HBr salt of 2N-isopropylamino-1,2,3,4-tetrahydro-5,6-dihydroxynaphthalene.

The pharmaceutical compositions of this invention will contain the active compound together with a solid or liquid pharmaceutically acceptable nontoxic carrier. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerole solutions can also be employed as liquid carriers, particularly for injectable solutions. Suitable pharmaceutical excipients include starch, glucose, lactose, sucrose, gelatine, malt, rice, flour, chalk, silica gel, magnesium carbonate, magnesium stearate, sodium stearate, glycerol monostearate, talc, sodium chloride, dried skim milk, glycerol, propylene glycol, water, ethanol and the like. These compositions can take the form of solutions, suspensions, tablets, pills, capsules, powders, sustained-release formulations and the like. Suitable phamaceutical carriers are described in "Remington's Pharmaceutical Sciences" by E. W. Martin. Such compositions will contain an effective therapeutic amount of the active compound together with a suitable amount of carrier so as to provide the form for proper administration to the host. While intravenous injection is a very effective form of administration, other modes can be employed.

What is claimed is:

1. A method of producing smooth muscle tissue relaxation therapy in a mammal requiring such therapy which comprises internally administering to said mammal an amount effective to produce smooth muscle tissue relaxation, of a compound of the formula:

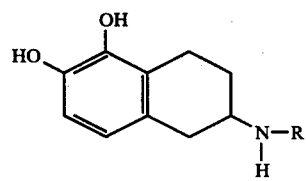

wherein R is alkyl having from 1 to 6 carbon atoms.

2. The method of claim 1 wherein R is methyl.

3. The method of claim 1 wherein R is isopropyl.

4. The method of claim 1 wherein the administration is oral.

5. The method of claim 1 wherein the administration is parenteral.

6. The method of claim 1 which comprises administering to the mammal a daily dosage of between about 5 µg/kg and about 10 mg./kg of mammal body weight.

7. The method of claim 1 wherein said compound is administered in an amount effective to relieve bronchial asthma.

8. The method of claim 1 wherein said compound is administered in an amount effective to produce relaxation of the uterine smooth muscle.

* * * * *